United States Patent [19]

Maender et al.

[11] 4,140,716

[45] Feb. 20, 1979

[54] PROCESS FOR MAKING AN AMIDE OF FORMIC ACID AND FORMING NITRODIARYLAMINE THEREFROM

[75] Inventors: Otto W. Maender, Copley; Gene R. Wilder, Medina, both of Ohio

[73] Assignee: Monsanto Company, St. Louis, Mo.

[21] Appl. No.: 867,091

[22] Filed: Jan. 5, 1978

[51] Int. Cl.$^2$ .................. C07C 102/00; C07C 85/04; C07C 85/153

[52] U.S. Cl. ....................... 260/562 R; 260/561 R; 260/562 A; 260/571; 260/576

[58] Field of Search ................ 260/576, 571, 562 R, 260/561 R

[56] References Cited

U.S. PATENT DOCUMENTS

| | | | |
|---|---|---|---|
| 1,777,777 | 10/1930 | Wietzel | 260/562 R |
| 3,393,241 | 7/1968 | Nielsen | 260/576 |

FOREIGN PATENT DOCUMENTS

| | | | |
|---|---|---|---|
| 498077 | 12/1953 | Canada | 260/576 |
| 1056619 | 5/1959 | Fed. Rep. of Germany | 260/576 |
| 1455207 | 11/1976 | United Kingdom | 260/576 |

OTHER PUBLICATIONS

Rondestvedt, "J. Org. Chem.", 42(10), pp. 1786–1790 (1977).
Sharnin et al., "J. Org. Chem. USSR", 6, pp. 990–992 (1970).
Bhattacharyya et al., "Chem. Ab.", 68, Ab. No. 21623z (1968).

*Primary Examiner*—Winston A. Douglas
*Assistant Examiner*—John Doll

[57] ABSTRACT

Use of alkali metal salts of the formyl derivatives of aromatic amines to initiate the formation of formamides from carbon monoxide and amines and conversion of the products to nitrodiarylamine are disclosed.

10 Claims, No Drawings

PROCESS FOR MAKING AN AMIDE OF FORMIC ACID AND FORMING NITRODIARYLAMINE THEREFROM

The invention relates to a process for making an amide of formic acid from carbon monoxide. The invention particularly relates to making the formyl derivative of a primary aromatic amine for conversion to nitrodiarylamine and one embodiment of the invention relates to making 4-nitrodiphenylamine starting with aniline and carbon monoxide. Nitrodiphenylamine is an important intermediate for rubber antidegradants.

Carbon monoxide combines directly with amines to form amides only with difficulty. It is necessary to employ a suitable catalyst or promoter to initiate the condensation in order to effect reasonable yields and reaction rates. For example, alkali metal alcoholates are known to initiate the condensation of carbon monoxide and amines to formamides Ya. Yu. Aliev and I. B. Romanova. Chemical Abstracts, 61 p. 6913 (1964). The present invention provides a new and improved system to initiate the formation of amides from amines and carbon monoxide and one which has special advantages as part of a process for making nitrodiarylamines.

It has now been discovered that the condensation of carbon monoxide and amines is initiated by an alkali metal salt of the formyl derivative of an amine in the presence of an alcohol, preferably methanol; but, generally, any lower alcohol of 1-5 carbon atoms may be used. Such discovery is significant to the synthesis of nitrodiarylamines because there may be selected as catalyst for initiating the condensation of the carbon monoxide and amine a precursor for the nitrodiarylamine. The process is of particular value where a salt of the resulting formamide is desired and especially where a mixture of the formamide and salt is required. Amines which are reactive in the process include primary and secondary amines such as the N-lower alkyl anilines, dialkylamines, especially lower dialkyl amines, cycloalkylamines such as cyclopentylamine and cyclohexylamine, N-alkylcycloalkylamines, alkylamines, aralkylamines such as benzylamine and aryl amines such as aniline and naphthylamine. The amine and alkali metal salt may be charged to a reactor in a ratio, for example, of about 9 to 10 moles of amine per mole of alkali metal salt together with the alcohol and carbon monoxide charged to the reactor under greater than atmospheric pressure.

To obtain catalyst to initiate the condensation, the alkali metal salts of N-formylaromatics may be prepared from the corresponding alkali metal alkoxides in dimethylformamide or xylene. The alcohol is constantly removed to drive the reaction to completion. When xylene is used, a suitable solvent for making sodium salts, the solid salt is allowed to separate under stirring. In dimethylformamide, a solution is present throughout and refractometer readings of the distillate are taken periodically until the refractive index of the higher boiling solvent is obtained.

Potassium formanilide believed to be a new compound may be prepared and isolated as follows: From 122 parts by weight (1.3 mole) of 45% potassium hydroxide, 300 parts by weight of butanol and 100 parts by weight of xylene, 1.3 mole of potassium butoxide is prepared by stripping out water into a suitable water trap. The potassium butoxide is then added to a slurry of 156 parts by weight of formanilide in 250 parts by weight of xylene at ambient temperature. The butanol, xylene slurry is distilled in vacuo (100 mm. Hg.) until the overhead refractive index is 1.497, xylene being added to maintain the volume. The slurry is cooled to ambient temperature and the vacuum released under nitrogen. The slurry is then filtered and the xylene replaced by benzene, always keeping a liquid layer over the cake. The benzene is replaced by hexane in the same fashion, the bulk of the hexane is pulled through and the cake quickly transferred to a suitable container and dried. One obtains a crystalline white product soluble in dimethylformamide, methanol and butanol. Potassium formanilide melts at 184°–186° C. An associated formanilide-K-formanilide adduct melts at 140°–145° C., and some samples of potassium formanilide will show both exotherms in differential scanning calorimetry.

Sodium formanilide may be prepared as follows:

To 41.6 grams of formanilide (0.35 mole) dissolved in 200 ml. of xylene is added dropwise under stirring at 80° C. under about 100 mm Hg. pressure 70.2 g. of 25% by weight sodium methoxide in methanol (0.325 mole). The methanol is distilled off followed by the higher boiling solvent in vacuo at a pot temperature below about 85° C. until the refractive index of the distillate is that of xylene (1.497). The solid sodium salt is separated by filtration and protected from moisture until ready for use.

Representatives of formanilides which may be made by the process of the invention are: formanilide, m-chloroformanilide, p-chloroformanilide, 2-methylformanilide, 3-methylformanilide, 4-methylformanilide, 3-ethylformanilide, 3,4-dimethylformanilide, 3-methoxyformanilide, 4-methoxyformanilide, 4-ethylformanilide, 4-isopropylformanilide, 4-butylformanilide, 3,4-dichloroformanilide and 4-nitroformanilide.

DESCRIPTION OF PREFERRED EMBODIMENTS

EXAMPLE 1

Formanilide

Into a 1-liter Parr autoclave equipped with an agitator, thermowell, rupture disc and cooling coils are placed 84 g. (0.9 mole) of aniline, 16 g. (0.1 mole) of potassium formanilide and 150 g. of methanol. The autoclave is closed and purged with CO. The temperature is raised to 100° C. with atm. steam and CO is introduced at 28 kg/cm$^2$ pressure. Absorption is rapid and little or no heat of reaction is noted. The reaction is run for 3½ hours, the autoclave cooled to 15° C., and the excess CO vented. The methanol is removed by distillation, xylene added and resulting xylene solution washed with 10 ml. of conc. hydrochloric acid and 200 ml. of water. The organic layer is separated and analyzed by gas-liquid chromatography. The yield of formanilide expected is approximately 93%.

EXAMPLE 2

Formanilide

To the reactor described in Example 1, there is placed 84 grams (0.9 mole) of aniline, 14 grams (0.1 mole) of sodium formanilide and 150 grams of methanol. The autoclave is closed and purged with carbon monoxide. The temperature of the autoclave is raised to 100° C. with atmospheric steam and carbon monoxide introduced at 28 kg/cm$^2$ pressure for 3½ hours. The reaction mixture is then cooled and vented, and the methanol removed by distillation. Xylene is added and the xylene solution washed with 0.1 moles hydrochloric acid to hydrolyze the sodium formanilide and the organic layer separated. Analysis shows that the yield of formanilide is about 86%.

EXAMPLE 3

N-Cyclohexylformanilide

To the reactor described in Example 1, there is placed 99 grams cyclohexylamine, 14 grams (0.1 mole) of sodium formanilide and 150 grams of methanol. The autoclave is closed and purged with carbon monoxide, the temperature raised to 100° C. with atmospheric steam and carbon monoxide introduced at 28 kg/cm$^2$ for about an hour. The reaction mixture is then cooled and vented, 10 milliliters of concentrated hydrochloric acid is added and the solvent is removed by distillation. Benzene is then added and the benzene solution filtered through a bed of filter acid. Distillation gives N-cyclohexyl formamide, boiling point 118°–130° C. at 3 milliliters. The expected yield is about 79%.

EXAMPLE 4

N-Methylformanilide

To the reactor described in Example 1 is charged 107 grams (1.0 mole) of N-methyl aniline, 14 grams (0.1 mole) of sodium formanilide and 150 milliliters of methanol. The autoclave is closed, purged with carbon monoxide and the temperature raised to 100° C. with atmospheric steam. Carbon monoxide is then introduced at 28 kg/cm$^2$ pressure for about 30 minutes. The basic reaction mixture is neutralized with hydrochloric acid and extracted with xylene. Gas liquid chromatographic analysis shows that a high conversion to N-methyl formanilide is obtained.

Adaptation of the aforedescribed reaction to the preparation of nitrodiarylamines provides a highly efficient process. In general, after completing the condensation of an aromatic primary amine and carbon monoxide to the formyl derivative of the amine, the latter is converted in whole or in part to its sodium, potassium, rubidium or cesium salt by a suitable salt-forming agent. A portion of the product is recycled to the carbon monoxide reactor for initiating another condensation with aromatic primary amine. The other portion of the product is reacted with nitrohaloarene containing reactive halogen and by-product carbon monoxide recycled to the carbon monoxide reactor.

For the reaction of p-nitrochlorobenzene and a salt of formanilide, the potassium salt is advantageously used in a molar ratio of 1.0 to 1.5 moles per mole of p-nitrochlorobenzene, and more preferably 1.2 to 1.4 moles. Although unnecessary, it is also preferred that, in addition to the potassium salt, formanilide be present in the reaction mixture. The molar amount of formanilide charged may be equal to or greater than the molar amount of potassium formanilide; but to minimize recovery problems and maximize production per unit volume, lower amounts are advantageous. The preferred range is 0.2–0.7 mole of formanilide per mole of p-nitrochlorobenzene, and more preferably 0.4–0.5 mole. The formanilide serves as polar solvent and reaction promoter. The preferred reaction temperature is 155°–165° C.

The sodium salt of formanilide is more economical than the potassium salt and is activated by sufficiently high proportions of the formanilide to produce good yields of 4-nitrodiphenylamine without resorting to expensive special polar solvents such as dimethylformamide. In general, for reacting sodium formanilide, formanilide and p-nitrochlorobenzene, it is desirable to use 1.0–1.5 moles of sodium formanilide and 0.4–2.6 moles of formanilide per mole of p-nitrochlorobenzene, preferred proportions being about 1.3 moles of sodium formanilide and about 1.3–1.6 moles of formanilide per mole of p-nitrochlorobenzene. The reaction rates and yields from sodium formanilide are excellent when the mole ratio of formanilide is equal to or exceeds 1, preferably 1–2, and the mole ratio of formanilide to p-nitrochlorobenzene is equal to or exceeds 1.3, preferably 1.3–2.6. The reaction temperature will be about 20°–25° C. higher for the sodium salt than for the potassium salt. Any inert solvent, if used, should be kept at a minimum, because of adverse effect on the reaction rate. The high formanilide level almost eliminates the formation of 4,4'-dinitrotriphenylamine, but the amount is increased several fold when dimethylformamide replaced formanilide.

The best mode presently known for preparing 4-nitrodiphenylamine using potassium formanilide to initiate condensation to the formanilide intermediate comprises charging aniline, methanol and reaction initiating amounts of potassium formanilide to an autoclave and feeding in carbon monoxide to form formanilide, coverting the formanilide produced to potassium formanilide or preferably to a mixture of potassium formanilide and formanilide in molecular proportion of 0.15–0.55 mole of formanilide per mole of potassium formanilide, recycling a portion of the mixture to the autoclave, removing methanol from the remainder, adding p-nitrochlorobenzene in a molecular proportion of 0.5 to 1.0 mole per mole of potassium formanilide and forming 4-nitrodiphenylamine, preferably at 155–165° C. By-product carbon monoxide is recycled to the autoclave.

The best mode presently known for preparing 4-nitrodiphenylamine using sodium formanilide to initiate condensation to the formanilide intermediate comprises charging aniline, methanol and reaction initiating amount of sodium formanilide to an autoclave and feeding in carbon monoxide to form formanilide, converting the formanilide produced to a mixture of sodium formanilide and formanilide in molecular proportion of 0.25–2.0 mole of formanilide per mole of sodium formanilide, recycling a portion of the mixture to the autoclave, removing methanol from the remainder, adding p-nitrochlorobenzene in molecular portion of 0.5 to 1.0 mole per mole of sodium formanilide and forming 4-nitrodiphenylamine, preferably at 150°–205° C.

When a sodium salt is the reactant for the nitrodiarylamine condensation, it is advantageous to add a reaction-promoting amount of a compound of potassium, cesium or rubidium or mixture thereof effective for promoting the reaction. In such compounds, the anion of the promoter appears to be largely a matter of choice examples being halogen, carbonate, bicarbonate, sulfate or acyl such as formate, acetate and benzoate or the anion from the formyl derivative of an aromatic primary amine. The molar ratio of the promoter for the 4-nitrodiphenylamine condensation is usually 0.025–1.0 mole equivalent; and, preferably, 0.5 to 0.7 mole equivalent of metal per mole of p-nitrochlorobenzene. Only small amounts of polar solvent are needed to show the aforesaid promoter action.

The following are illustrative of nitrohaloarenes which may be reacted with formyl derivatives of aromatic amines to form nitrodiarylamines: o-nitrochlorobenzene, o-nitrobromobenzene, p-nitrochlorobenzene, p-nitrobromobenzene, m-nitrochlorobenzene, m-nitrobromobenzene, 1-chloro-2-methyl-4-nitrobenzene, 1-chloro-3-methyl-4-nitrobenzene, 1-chloro-2-nitronaphthalene, 3,4-dichloronitrobenzene, 3-methyl-4-chloronitrobenzene, 2-methyl-4-chloronitrobenzene, 2-ethyl-4-chloronitrobenzene, 2,3-dimethyl-4-chloronitrobenzene, 2,5-dimethyl-4-chloronitrobenzene, 3,5-dimethyl-4-chloronitrobenzene and p-fluoronitrobenzene.

The 4-nitrodiphenylamine reaction may be carried out in mild steel, stainless steel, glass or glass-lined vessels and the carbon monoxide evolved recycled to the formanilide maker which will be a pressure vessel. Since a high purity CO is evolved uncontaminated with $CO_2$, recycling it to form more formanilide is feasible. After the condensation reaches the selected end-point, the alkali metal halide by-product may be removed by water washing; solvent removed by distillation, and the residue cooled to about 5° C. to recover 4-nitrodiphenylamine by crystallization.

The following example illustrates the process of preparing 4-nitrodiphenylamine starting with aniline and carbon monoxide.

Although the formation of alkali metal formanilide is illustrated by use of sodium methylate, other methods of making the salt may be employed. Other ways of making the sodium salt, such as by use of metallic sodium, sodium hydride or sodamide are available or may be developed which may be preferred to the sodium methylate route. When the formanilide is desired simply as an intermediate for its sodium salt, it will be appreciated that the formation of such salt generates catalyst for making the intermediate. Conversely, the use of sodium methylate to initiate formation of the intermediate requires a separate source of catalyst and mitigates against the feasibility of other methods for making the salt which might be preferred if sodium methylate were not required in the first step.

EXAMPLE 5

There is charged to the autoclave described in Example 1 120 grams (1.29 moles) of aniline, 23 grams (0.16 moles) of sodium formanilide and 190 grams of methanol. The autoclave is closed, purged with carbon monoxide and carbon monoxide introduced for 4 hours at 60°–65° C. under a pressure of 28 kg/cm$^2$. About 108 grams (0.50 mole) of 25% sodium methylate is added to convert a portion of the formanilide formed to sodium formanilide. There is then added 150 ml. of xylene and the methanol is removed in vacuo at about 60°–70° C., leaving as the residue a mixture of formanilide and sodium formanilide in xylene. To the residue is added 78.5 grams (0.5 mole) of p-nitrochlorobenzene and 18 grams of potassium chloride. A gas meter is attached to the reactor and a two-plate column. The reaction mixture is heated and xylene removed by distillation to a pot temperature of 170° C. Heating at 170° C. is then continued for about 2½ hours, during which time 21.1 liters of gas are collected. The reaction mixture is cooled to 140° C. and 150 milliliters of xylene added. The xylene solution is washed with hot water at 90° C., the organic layer separated, cooled to 5°–10° C., and filtered. The crystalline 4-nitrodiphenylamine on the filter is washed with xylene and dried to obtain 71.5 grams of product. The mother liquor contains another 29.4 grams. In particular, it contains 9.86% aniline, 13.6% formanilide, 1.32% diphenylformamidine and 7.6% 4-nitrodiphenylamine but only traces of para-nitrochlorobenzene. Conversion of p-nitrochlorobenzene is 100%, and yield 94.2%.

To adapt the above procedure to recycling, about 25% of the mixture of sodium formanilide and formanilide in methanol formed before the addition of xylene is recycled to the formanilide maker to provide catalyst for the next batch and the collected carbon monoxide is also recycled to the formanilide maker. The potassium chloride may be replaced by other promoters, for example, cesium chloride, rubidium carbonate, potassium acetate, potassium benzoate, potassium sulfate or potassium bromide. Strong alkalis foster side reactions and potassium hydroxide and tripotassium phosphate give poor results. Although the promoting effect of the metal may in some instances be obscured by adverse effects of the anion, a simple experiment or two will show whether a given potassium, cesium or rubidium compound is effective for promoting the reaction.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. In the process of making an amide of formic acid by condensation of carbon monoxide and primary amine, the improvement which comprises initiating the condensation by a mixture of alkali metal salt of the formyl derivative of a primary amine and a lower alcohol.

2. The process of claim 1 in which the alkali metal is sodium, potassium, cesium or rubidium, the amine is aniline or aniline substituted by one or more alkyl, alkoxy, fluoro or chloro substituents and the alcohol contains less than six carbon atoms.

3. The process of claim 1 in which the alkali metal is sodium, the amine is aniline and the alcohol is methanol.

4. The process of claim 2 in which the amine and alkali metal salt are charged to a reactor in a ratio of about 9 to 10 moles of amine per mole of alkali metal salt together with the alcohol and carbon monoxide charged to the reactor under greater than atmospheric pressure.

5. The process of forming nitrodiarylamine which comprises initiating condensation of carbon monoxide with a primary amine which is aniline or aniline substituted by one or more alkyl, alkoxy, fluoro or chloro substituents to the formyl derivative of said primary amine by a mixture of lower alcohol and alkali metal salt of the formyl derivative of the primary aromatic amine to be formed, converting the said formyl derivative to alkali metal salt, removing the alcohol and then, without isolating the alkali metal salt, reacting it with nitrohalobenzene, the said alkali metal being sodium, potassium, cesium or rubidium.

6. The process of claim 4 wherein the alkali metal is potassium and the nitrohalobenzene is p-nitrochlorobenzene.

7. The process of claim 4 wherein the alkali metal is sodium and the nitrohalobenzene is p-nitrochlorobenzene.

8. The process of forming nitrodiphenylamine which comprises initiating reaction of carbon monoxide and aniline in a pressure vessel with reaction-promoting amounts of potassium formanilide and methanol, converting formanilide produced to a mixture of potassium formanilide and formanilide in molecular proportion of 0.15–0.55 mole of formanilide per mole of potassium formanilide, recycling a portion of the mixture to the pressure vessel, removing methanol from the remainder, adding p-nitrochlorobenzene in a molecular proportion of 0.5 to 1.0 mole per mole of potassium formanilide and forming 4-nitrodiphenylamine.

9. The process of forming nitrodiphenylamine which comprises initiating reaction of carbon monoxide and aniline in a pressure vessel with reaction-promoting amounts of sodium formanilide and methanol, converting formanilide produced to a mixture of sodium formanilide and formanilide in molecular proportion of 0.25–2.0 mole of formanilide per mole of sodium formanilide, recycling a portion of the mixture to the pressure vessel, removing methanol from the remainder adding p-nitrochlorobenzene in molecular portion of 0.5 to 1.0 mole per mole of sodium formanilide and forming p-nitrodiphenylamine.

10. The process of claim 9 wherein the reaction to form p-nitrodiphenylamine is conducted in the presence of a reaction-promoting amount of potassium chloride.

* * * * *